United States Patent
Remes et al.

(10) Patent No.: US 11,197,629 B2
(45) Date of Patent: Dec. 14, 2021

(54) METHOD AND PORTABLE MONITORING MODULE FOR MONITORING A PLURALITY OF ELECTRICAL BIOSIGNALS OF A PERSON

(71) Applicant: Bittium Biosignals Oy, Kuopio (FI)

(72) Inventors: Arto Remes, Kuopio (FI); Santtu Remes, Kuopio (FI); Simo-Pekka Simonaho, Kuopio (FI); Juha Kylliäinen, Siilinjärvi (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 526 days.

(21) Appl. No.: 16/008,857

(22) Filed: Jun. 14, 2018

(65) Prior Publication Data

US 2018/0360337 A1 Dec. 20, 2018

(30) Foreign Application Priority Data

Jun. 15, 2017 (FI) .................................... 20175559

(51) Int. Cl.
*A61B 5/316* (2021.01)
*A61B 5/00* (2006.01)
(Continued)

(52) U.S. Cl.
CPC ............ *A61B 5/316* (2021.01); *A61B 5/0006* (2013.01); *A61B 5/0205* (2013.01); *A61B 5/366* (2021.01);
(Continued)

(58) Field of Classification Search
CPC . A61B 5/04015; A61B 5/0006; A61B 5/0205; A61B 5/04012; A61B 5/0472;
(Continued)

(56) References Cited

U.S. PATENT DOCUMENTS 5,311,876 A 5/1994 Olsen et al.
5,776,057 A 7/1998 Swenson et al.
(Continued)

FOREIGN PATENT DOCUMENTS

EP 1 070 479 A2 1/2001
EP 1 815 784 A1 8/2007
(Continued)

OTHER PUBLICATIONS

FI Search Report, dated Jan. 12, 2018, from corresponding FI20175559 application.

(Continued)

*Primary Examiner* — Aaron F Roane
(74) *Attorney, Agent, or Firm* — Nixon & Vanderhye (57) ABSTRACT

Disclosed is a portable monitoring module and a monitoring method utilizing the module for monitoring a plurality of electrical biosignals of a person. The module includes a measurement for measuring an electrical biosignal from the at least two electrodes, a wireless communication unit, and a processing unit. The processing unit selects a biosignal type to be monitored from a list of types supported by the monitoring module, store samples of biosignal data generated by the measurement unit, detect an indicator pattern within the biosignal data, wherein the indicator pattern represents an indication of a possible event of the selected biosignal type, and send a set of biosignal data wirelessly to a validation system. The set of biosignal data represents a sequence of samples of biosignal data related to the detected indicator pattern, and the validation system confirms the presence of the event in the received set of biosignal data.

11 Claims, 5 Drawing Sheets

(51) Int. Cl.
*A61B 5/366* (2021.01)
*A61B 5/389* (2021.01)
*A61B 5/0205* (2006.01)
*A61B 5/291* (2021.01)
*A61B 5/352* (2021.01)

(52) U.S. Cl.
CPC ............ *A61B 5/389* (2021.01); *A61B 5/7282* (2013.01); *A61B 5/0022* (2013.01); *A61B 5/291* (2021.01); *A61B 5/352* (2021.01); *A61B 5/4082* (2013.01)

(58) Field of Classification Search
CPC ... A61B 5/0488; A61B 5/7282; A61B 5/0022; A61B 5/0456; A61B 5/0478; A61B 5/4082
USPC ......................................................... 600/519
See application file for complete search history.

(56) References Cited

U.S. PATENT DOCUMENTS

| | | | |
|---|---|---|---|
| 6,441,747 B1* | 8/2002 | Khair | A61B 5/061 340/870.16 |
| 8,019,402 B1 | 9/2011 | Kryzpow et al. | |
| 2013/0095459 A1 | 4/2013 | Tran | |
| 2013/0158422 A1 | 6/2013 | Zhang | |
| 2014/0257129 A1 | 9/2014 | Choi et al. | |
| 2014/0316230 A1* | 10/2014 | Denison | A61B 5/4094 600/383 |
| 2016/0120434 A1* | 5/2016 | Park | A61B 5/046 600/301 |
| 2016/0361024 A1 | 12/2016 | Chakravarthy et al. | |
| 2017/0156662 A1* | 6/2017 | Goodall | A61B 5/0036 |

FOREIGN PATENT DOCUMENTS

| | | |
|---|---|---|
| WO | 0178831 A2 | 10/2001 |
| WO | 2006/008334 A1 | 1/2006 |
| WO | 2009033374 A1 | 3/2009 |
| WO | 2015/084899 A1 | 6/2015 |

OTHER PUBLICATIONS

Extended European Search Report issued in European Patent Application No. 18174563.9 dated Nov. 15, 2018.

\* cited by examiner

METHOD AND PORTABLE MONITORING MODULE FOR MONITORING A PLURALITY OF ELECTRICAL BIOSIGNALS OF A PERSON

FIELD

The present invention relates to monitoring of electrical biosignals, and more particularly to a wearable system and automatic algorithms for detecting abnormal physiological signals from human body in order to help medical decision making.

BACKGROUND

All functions of a human body are controlled by a central nervous system. Body metabolism maintains human cells in working condition by providing them with nutrients for the process of creating the necessary energy and building materials. In a healthy body, the entire system functions well while electrical biosignals of the body indicate normal operation of the necessary processes of the body.

Abnormalities or disturbances in the processes of the body may often be detected as reflecting pain, tiredness, lack of appetite, or strange behaviour etc. In order to find the cause of these symptoms, a medical examination is typically performed. A medical examination may include taking body samples, such as blood, urine, cell samples, and/or performing medical imagining. In case of neuro-physiological symptoms, electrical biosignals of human body may be monitored and analysed. In order to measure an electrical biosignal, the person whose biosignal is measured may be equipped with electrodes attached to the body of the person. Electro-myography (EMG), electrocardiogram (ECG), and electroencephalogram (EEG) are some examples of electrical biosignals.

Electromyography (EMG) is an electrophysiological monitoring process for evaluating and recording the electrical activity produced by skeletal muscles.

Electromyography gives electrical feedback from voluntary muscle functions and, with external electrical stimulation responses, gives feedback about neuro-muscular functionality. Normal or abnormal nerve conduction can be detected by stimulating nerves with electrical pulse and measuring same time the delays to get motoric unit potential from another point of the body with a known distance.

Electrocardiography (ECG) is the process of recording the electrical activity of the heart over a period of time using electrodes placed on the skin. These electrodes detect the tiny electrical changes on the skin that arise from the heart muscle's electrophysiologic pattern of depolarizing and repolarizing during each heartbeat.

Electroencephalography (EEG) is an electrophysiological monitoring method to record electrical activity of the brain. It is typically non-invasive, with electrodes placed along the scalp, although invasive electrodes are sometimes used in specific applications. EEG measures voltage fluctuations resulting from ionic current within the neurons of the brain.

Detection and interpretation of electrical biosignals can be challenging as the biosignals may have complicated characteristics. The characteristics of different types of electrical biosignals may be very different from each other. Further, the characteristics of the biosignals may vary person to person.

BRIEF DISCLOSURE

An object of the present invention is to provide a method and an apparatus for implementing the method so as to alleviate the above disadvantage. The objects of the invention are achieved by a method and an arrangement which are characterized by what is stated in the independent claims. The preferred embodiments of the invention are disclosed in the dependent claims.

The present disclosure describes a portable (i.e. lightweight and wearable) monitoring module which may be provided with integrated, automated algorithms for detecting biosignal events (e.g. irregular and abnormal electrical signal episodes from brain, heart or muscles). The algorithms may be configured to produce indications of possible biosignal events by calculating changes in linear and non-linear parameters in electrical biosignals. The monitoring module may comprise high accuracy amplifiers for 1-64 measurement channels, an anti-aliasing filtering unit, a microprocessor, a memory for long term recording (e.g. >1 Gbyte), a wireless Bluetooth or WLAN module, led/display indicators, a rechargeable battery and an USB or similar wired link, for example. The frequency band, gain, sampling rate and configuration of measurement channels of the monitoring module may be configurable in order to enable measurement of different various types of electrical biosignals, such as ECG, EMG and ECG.

The portable monitoring module may be a part of a larger monitoring system. Based results generated by the algorithms, the module may provide a subsequent validation system with sampled biosignal data related to a detected possible biosignal event. The validation system may then validate the biosignal data against a reference database in order confirm the detection sensitivity and specificity.

With the above-described setup, electrical biosignals of a monitored person may be reliably detected while maintaining the freedom of movement of the person. The module enables uninterrupted, around-the-clock wireless monitoring without a need for changing the monitoring device. Early detection of hidden cardiac abnormalities improves the chances of preventing cardiac failures such as heart attacks, stroke and in the worst case sudden death.

A plurality of different electrical biosignals may be monitored with a single portable monitoring module. Since the module may be configured to send data only when a possible event is detected, and since the algorithms detecting the possible events are computationally light, a very long operational time of the module can be achieved.

The validation system may perform the confirmation of the presence (or lack of presence) of a biosignal event. Computationally intensive calculation, such as interpretation of the biosignal, may be implemented as a cloud service, for example. With mobile tools, the cloud service also enables easy access to biosignal data for both neurologist and bed space personnel.

BRIEF DESCRIPTION OF THE DRAWINGS

In the following the invention will be described in greater detail by means of preferred embodiments with reference to the attached drawings, in which.

DETAILED DISCLOSURE

The present disclosure describes a portable monitoring module for monitoring electrical biosignals of a person. In the context of the present disclosure, a portable module is intended to be understood as a lightweight module that can be worn as a garment. An electrical biosignal is in this context a signal representing a measurable electric variable of a living being. Electromyography (EMG), electrocardiogram (ECG), and electro-encephalogram (EEG) are examples of such electrical biosignals. The term electrical biosignal is not, however, limited to these examples.

The portable monitoring module comprises a measurement unit configured to measure an electrical biosignal from the at least two electrodes, a wireless communications unit (i.e. a wireless unit), and a processing unit. The measurement unit of a monitoring module according to the present disclosure may comprise one or more signal amplifiers and one or more A/D converters. The gain and/or anti-aliasing filtering of the signal amplifier and the sampling rate of the A/D converter may be adjustable. In this context, terms "adjustable" and "configurable" should be understood as something that can be adjusted or changed to a different value in response to a control signal during use. Further, the number and configuration of active channels to be measured may be adjustable in the measurement unit. The measurement unit may comprise selection means (e.g. selection electronics comprising analog multiplexers) for selecting desired sets of channels for different measurements.

The processing unit may comprise a processor coupled with a memory, for example. The processing unit may be configured to select a biosignal type to be monitored from a list of electrical biosignal types supported by the monitoring module. The portable monitoring module may comprise a selector (e.g. a switch) for selecting the biosignal type, and/or the processor unit of the module may receive a biosignal type selection signal from an external system. The processor unit may also be configured to automatically detect the present configuration of electrodes attached to the portable monitoring module and make the selection of the biosignal type on the basis of the detected present configuration.

Based on the selected biosignal type, the processing unit may select active channels to be measured and set up the gain and filtering of the signal amplifier and the sampling rate of the A/D converter. The processing unit may then store samples of biosignal data generated by the measurement unit, and detect an indicator pattern within the biosignal data. The indicator pattern may represent an indication of a possible event of the selected biosignal type. An event may represent an episode of abnormal physiological signals from human body.

The processing unit may be configured such that, when indicator pattern is detected, the monitoring module sends a set of biosignal data via the wireless communications unit to be received by a validation system. The set of biosignal data may represent a sequence of samples of biosignal data related to the detected indicator pattern. The validation system may then confirm the presence of the event in the received set of biosignal data.

A portable monitoring module according to the present disclosure may be configured to monitor a plurality of electrical biosignals. The list of measured biosignal types supported by the module may include electrocardiography (ECG), electroencephalography (EEG), and electromyography (EMG), for example.

In the following, some monitoring algorithms for detecting possible electrical biosignal events in real time are discussed in more detail.

For example, in a first aspect of a portable monitoring module according to the present disclosure, the processing unit of the portable monitoring module may include an algorithm that automatically detects QRS complexes from ECG signal. The algorithm may be further configured to detect and mark arrhythmias, such as Pause (i.e. skipped heart beats), Bradycardia (i.e. low pulse rate), Tachycardia (i.e. high pulse rate) and Atrial fibrillation (i.e. irregularity between QRS sessions). The algorithms may be based on linear, non-linear, and/or frequency-based calculation.

Figure 1A:
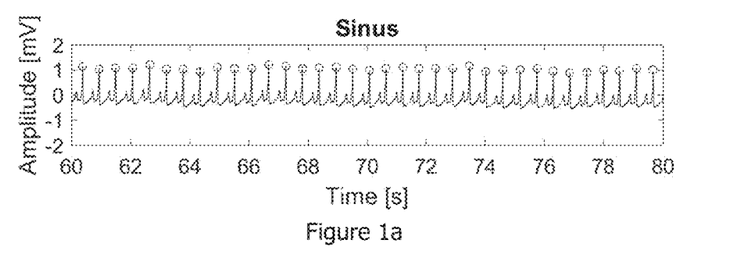
FIG. 1a shows an example of normal sinus rhythm.
Figure 1B:
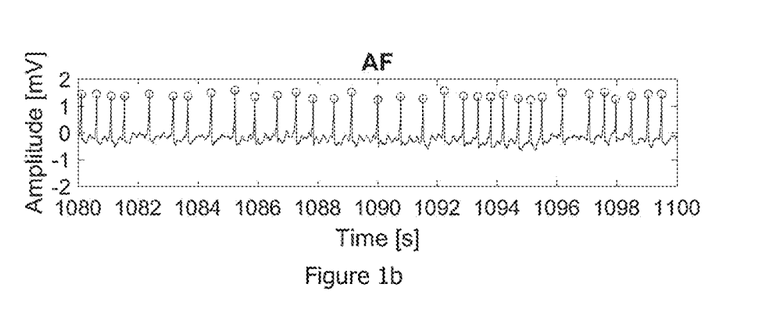
FIG. 1b shows and example of atrial fibrillation.

For example, the portable monitoring module may comprise an algorithm for detecting an indication pattern indicating possible atrial fibrillation in real time. Normal heart rhythm follows so-called sinus rhythm which is generated by the sinus node (i.e. sinoatrial node). The sinus rhythm in turn follows respiration. FIG. 1a shows an example of normal sinus rhythm. If the heart loses the rhythm driven by sinus node, the left atrium of the heart takes role of creating heart left ventricular contraction. In this case, left atrium starts to fibrillate irregularly. This phenomena is called atrial fibrillation. FIG. 1b shows an example of abnormal behaviour of heart. In FIG. 1b, an irregular rhythm of ECG can be seen as atrial fibrillation is actively disturbing the heart's normal function. If the phenomena continues for a prolonged time, blood may not move properly from the left atrium to the left ventricle and which increases the risk of blood clots being formed. Such clots may detach and start moving to through aorta and brain arteria to brain, thus creating high possibility of a stroke.

Figure 3A:
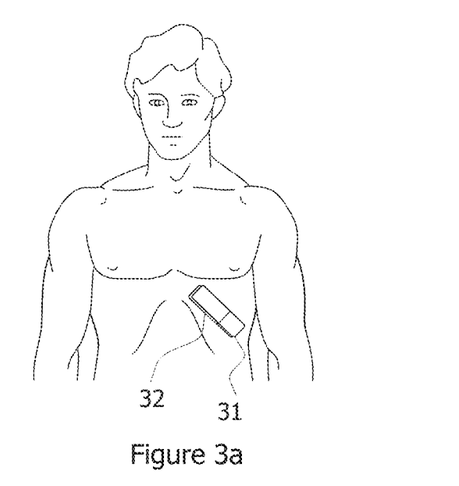
FIG. 3a shows an exemplary arrangement for measuring ECG of a person.

In order to detect atrial fibrillation, a galvanic connection or galvanic connections may be formed to the human chest with a single electrode patch, disposable electrodes or a dry electrode solution with a chest belt in order to detect ECG signal. Operation of the heart may be monitored for days or months at a time. FIG. 3a shows an exemplary arrangement for measuring ECG of a person. In FIG. 3a, a portable monitoring module 31 according to the present disclosure is attached to a sensor module 32 comprising electrodes attached to the chest of the person.

The processing unit of a monitoring module according to the present disclosure may be configured to analyse a sequence of successive samples of ECG data in order to detect QRS complexes (or at least specific elements of QRS complexes). The sequence may represent samples of ECG data for a time window of last 60 seconds, for example. However, the time window may also be set to be less or more than 60 seconds.

For the sequence of successive samples of ECG data, intervals between successive QRS complexes within the samples of ECG data may be determined, and deviations between each two successive intervals may be calculated. A cumulative sum of the deviations may be calculated, and if the cumulative sum exceeds a set limit, an indication signal indicating a possible atrial fibrillation may be generation. In the context of the present disclosure, the term "successive QRS complexes" refers to QRS complexes that are consecutive, i.e. immediately successive, and the phrase "each two successive intervals" refers to a first interval between a first QRS complex and a second QRS complex that is immediately successive to the first QRS complex and a second interval between the second QRS complex and an third QRS complex that is immediately successive to the second QRS complex. The intervals may be determined by detecting specific elements of QRS complexes. In some embodiments, an R peak of a QRS complex may be detected as a peak amplitude within the ECG signal data or as a rate of change exceeding a set limit, for example.

Figure 2:
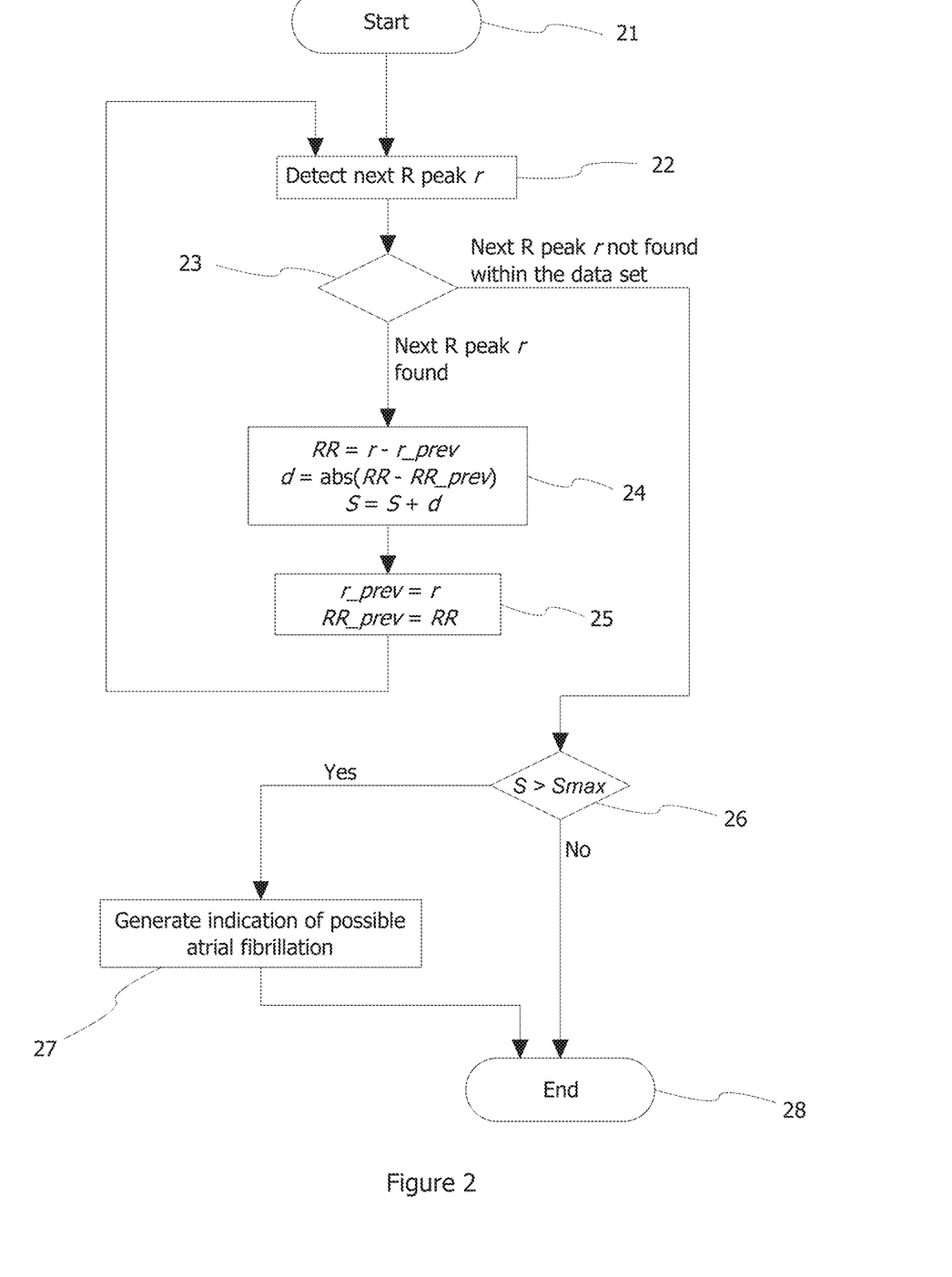
FIG. 2 shows a simplified flow chart of an exemplary embodiment of an algorithm for detecting atrial fibrillation.

FIG. 2 shows a simplified flow chart of an exemplary embodiment of an algorithm for detecting atrial fibrillation. After entering the algorithm at starting step 21, the algorithm tries to find the next R peak r as the indicator of the next QRS complex. In step 23, if a R peak is found, the algorithm continues to step 24.

In step 24, the algorithm calculates an interval RR between two successive R peaks, i.e. the newest R peak r and its immediate predecessor r_prev. The interval may be calculated as a difference between the positions of said two peaks in a time scale, for example. Further in step 24, a deviation d between the interval RR and its immediate predecessor RR_prev is calculated. In FIG. 2, the deviation d is in the form of an absolute value of the difference between said two successive intervals RR and RR_prev. A cumulative sum S is also calculated in step 24. The algorithm then returns to step 22 to detect the next R peak. The cycle of steps 22 to 25 is repeated until new R peaks are no longer found in the data set. At each cycle, the new value of the deviation d is added to the cumulative sum S. When no new R peaks are found, step 23 continues to step 26 where the value of the cumulative sum S is compared to a set limit Smax. If the value of the cumulative sum does not exceed the set limit Smax, the algorithm reaches its end at step 28. However, if the sum S exceeds the set limit Smax, the algorithm in FIG. 2 continues to step 27, where an indication of possible atrial fibrillation is generated.

The processing unit may also be configured to detect other arrhythmias from the ECG data. For example, the processing unit may also detect Pause (i.e. skipped heart beats), Bradycardia (i.e. low pulse rate), Tachycardia (i.e. high pulse rate) based on the calculated intervals. If a calculated interval (or an average of invervals over a set time window) exceeds a set maximum limit, and indication of possible Tachycardia may be generated. In a similar manner, if a calculated interval (or an average of invervals over a set time window) falls below a set minimum limit, and indication of possible Bradycardia may be generated. An indication of Pause may be generated, if an interval exceeds an average of invervals over a set time window by a set percentage, for example. A portable monitoring module according to the present disclosure may further comprise pacemaker detection unit for detecting if a pacemaker is being used for controlling the heart rate. Pacemaker signals appear as high frequency pulses right before the ECG waveform. Thus, the pacemaker detection unit may be configured to detect high-frequency pulses. The pacemaker detection unit may be implemented as an electronic circuit or as software, for example. Indication the current status of the pacemaker may be sent to a validation system, for example.

Once a portable monitoring module according to the present disclosure detects a possible arrhythmia, it generates an indication signal of its findings. In its simplest form, the indication signal may be generated through a visual indicator, such as a LED or display, on the portable monitoring module. The indication signal may also be generated as an audio signal. For example, the monitoring module may generate a speaker or a connector for headphones through which the audio indicator signal is outputted.

Alternatively, or in addition, the indication signal may be forwarded to a subsequent validation system. Together with the indication signal, the monitoring module may send a set of biosignal data related to the detected arrhythmia via the wireless communications unit of module to be received by the validation system. The biosignal data may be wirelessly received by a communications device which may relay the data to the validation system over the internet, for example. The communications device may be a handheld computing device with wireless communications capabilities, such as a smart phone or a tablet computer, or a WLAN router, for example. The validation system may be implemented on a cloud computing system, for example. Alternatively, the handheld computing device may also act as the validation system.

The validation system may be configured to analyze the received biosignal data and confirm the presence (or lack of presence) of the monitored arrhythmia condition. Based on its analysis, the validation system may provide the biosignal data and other information to medical personnel, such as ECG technicians monitoring data flow of patients.

In order to further improve the reliability of the confirmation processing, the biosignal data received from the portable monitoring module may be compared with a reference database. The reference database may contain biosignal data of a person over a long period of time, e.g. weeks, months or even years. The reference database may receive data from monitoring modules of different persons. In this manner, the database may be taught to link certain characteristics of the received biosignal data to certain parameters of the monitored persons, such as gender, age, weight, illnesses, blood pressure, blood sugar, etc. The information provided by the portable monitoring module and the information provided by the validation system and/or the reference database help making right diagnosis based on the findings and providing the correct medication or other steps early on.

If a patient is found in unconscious state, it may be difficult to define whether the unconscious state was caused by stroke, intra cranial blood leakage or epileptic status. All these cases are serious brain problems that require immediate medical treatment and, in the worst case, may lead to the serious brain damage or even death. Therefore, a second aspect of a portable monitoring module according to the present disclosure is that the module is configured to measure EEG and detect epileptic seizures based on EEG data.

An epileptic seizure changes normal EEG signal. Thus, it is possible, with very high sensitivity, to indicate epileptic status with the help of smart algorithms and indicate the status to first aid staff, nurse or doctor, thereby allowing immediate medication to patient with a right dosage. This can accelerate the treatment process and help the patient to avoid brain damage or worse consequences even before entering hospital for getting complete treatment.

Figure 4:
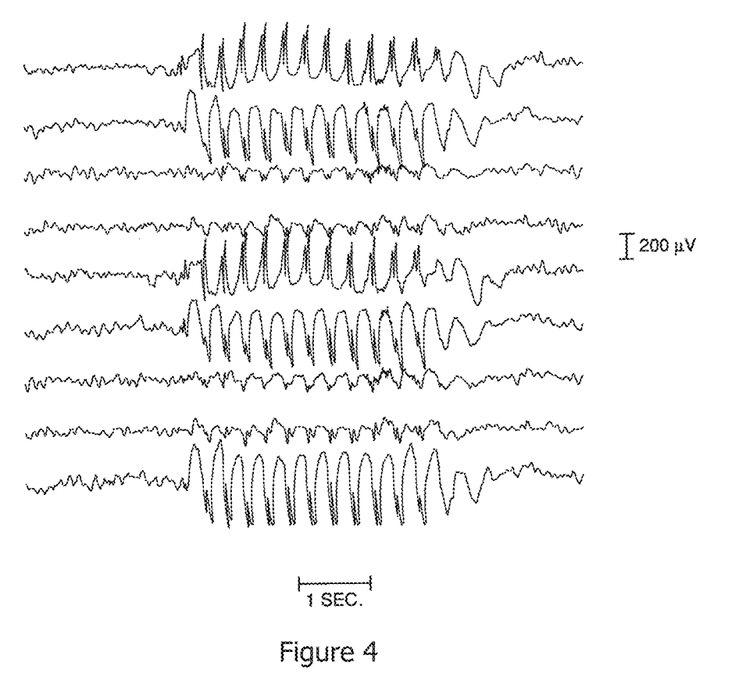
FIG. 4 shows an example of epileptic seizure observable in brainwaves of an EEG measurement.

The processing unit of a portable monitoring module according to the present disclosure may be configured to use linear and/or non-linear calculation on the EEG data in order to automatically detect an epileptic seizure in real time. Further, the processing unit may also determine amplitude or frequency content and/or change of the amplitude or the frequency content in order to detect the epileptic seizure. Brain EEG can normally be quite chaotic and, therefore, certain waveforms emerging in the EEG can be used for detecting a seizure. FIG. 4 shows an example of epileptic seizure observable in brainwaves of an EEG measurement. The seizure can be seen as a low-frequency periodic signal with increased signal amplitude compared with the normal period before and after the seizure. As shown in FIG. 4, signal amplitude increases and a signal burst appears in the EEG signal during an epileptic seizure. Therefore, the processing unit of a monitoring module may be configured to detect a change in the EEG data in order to determine presence of an epileptic seizure, wherein the change in the EEG data is in the form of a change in amplitude, rate of change or periodicity of a measured EEG signal. The frequency band of the EEG measurements may be the same as with the ECG.

Figure 3B:
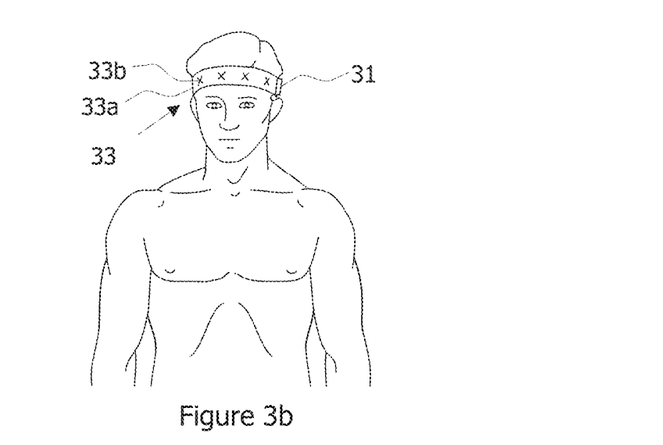
FIG. 3b shows an exemplary arrangement for measuring EEG of a person.

FIG. 3b shows an exemplary arrangement for measuring EEG of a person. In FIG. 3b, a portable monitoring module 31 according to the present disclosure is connected to an EEG sensor module 33. The portable monitoring module may be the same as in FIG. 3a, for example. The sensor module 33 comprises a headband 33a that has a plurality of electrodes 33b that are placed on the scalp of the person at suitable positions for EEG measurements. The measurement unit of the monitoring module 31 may be configured to have 4-64 EEG measurement channels, for example. Said channels may be connected to the electrodes of the sensor module 33. For example, the electrodes may be disposable, equipped with hydrogel, or they may be reusable, covered with AgCI gel or potassium-water liquid that contains ions for allowing electric transmission from skin to the measurement unit of the monitoring module 31.

Similar to the detection of arrhythmias of heart, the monitoring module according to the present disclosure may generate an indication signal when detecting a possible seizure. Together with the indication signal, the monitoring module may send a set of EEG data related to the detected seizure via the wireless communications unit to be received and confirmed by an automatic validation system or medical personnel, such as a neurologist. Similar to the previously described embodiment detecting arrhythmias, a reference database for EEG data may receive data from monitoring modules of different persons. In this manner, the reference EEG database may be taught to link certain characteristics of the received EEG data to certain parameters of the monitored persons, such as gender, age, weight, illnesses, blood pressure, blood sugar, etc.

A confirmation of a seizure may be indicated to medical staff and/or family members visually or with a sound alarm, for example. Information about the person's seizure can be also send via wired or wireless transfer to internet or other family members to their tablet, mobile phone or computer, and displayed in the form of colour-coded indications (e.g. a green, yellow, red or flashing red sign indicating different levels of severity of a seizure) or played as an audible alarm sound. With the confirmation of the seizure (and its severity) the medical personnel can start right medication already in the ambulance or medical helicopter in order to protect the brains from damage.

The monitoring module (and the reference database) may also be used for detecting other brain problems, such as a stroke and intra-cranial blood leakage.

In addition the above-described first and second aspect of the portable monitoring module according to the present disclosure, a third aspect of the module is that it may also be configured to measure EMG. The EMG measurement may be used for monitoring tremors of Parkinson's disease, for example.

In Parkinson's disease, information from brain motor cortex to muscles is disturbed due to deficit (i.e. low levels) of dopamine which is an important neurotransmitter that transmits the data between neurons and brings motoric information the motor cortex of the brain. Dopamine has an important role in mood control of the human. Drug and alcohol abuse may also severely disturb the mood control and lead to the deep depression and mental problems. However, in distinction to symptoms related to drug and alcohol abuse, patients affected by Parkinson's disease typically have asymmetrical tremors in their limbs, e.g. tremors in only one hand or leg. A tremor caused by Parkinson's disease may be in the form of a rhythmic alternating pattern of contraction and relaxation in opposing muscles affected by tremor. The tremors are caused by the deficit of dopamine and are typically at their maximum when the patient is at rest. The tremors may become stronger and stronger as the disease progresses. Persons that are not affected by Parkinson's disease can control his muscle very smoothly, and their muscles are not activated while the persons are at rest.

When Parkinson's disease starts to progress, the EMG signal becomes less informative as the muscle control is disturbed by the deficit of dopamine. Further, a tremor may be observed as a strong frequency component in the EMG. Information contents of the EMG signal of a person affected by tremor caused by Parkinson's disease becomes more monotonic and less chaotic. The information contents and monotonicity of an EMG signal can be evaluated based on the number and magnitude of different frequency components observable in the EMG signal, for example.

Therefore, a portable monitoring module according to the present disclosure may be configured to monitor EMG of the person, and the processing unit may be configured to detect of an indicator pattern indicating a presence of a tremor in real time, even if the tremor would not otherwise be observable. The detection of the indicator pattern may comprise detecting a change in monotonicity of the EMG data in order to detect a tremor caused by Parkinson's disease. By calculating and monitoring frequency parameters and non-linear parameters of the EMG signal, symptoms, such as tremors, caused by Parkinson's disease can be detected in the EMG signal. Based on the presence (or non-presence) of tremors in a patient, timing and dosage of dopamine medication of the patient can be adjusted. The monitoring module may be configured such, that when it detects an abnormal signal, it sends an indication signal to an automated medication dispenser thereby indicating the right time for taking the prescribed medication.

Figure 3C:
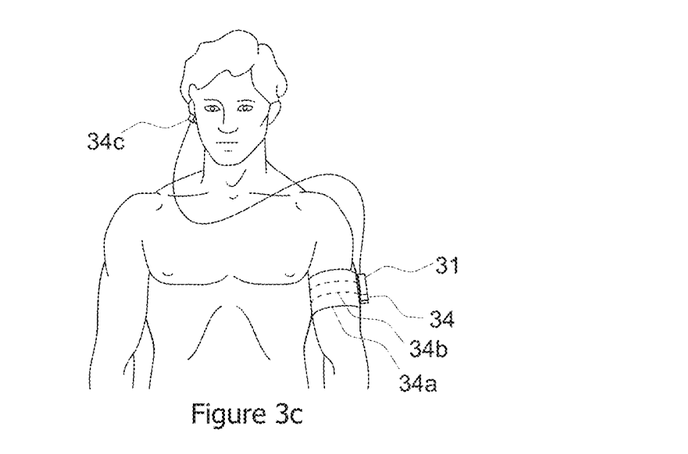
FIG. 3c shows an exemplary arrangement for measuring EMG of a person.

FIG. 3c shows an exemplary arrangement for measuring EEG of a person. In FIG. 3c, a portable monitoring module 31 according to the present disclosure is connected to an EMG sensor module 34. The portable monitoring module may be the same as in FIGS. 3a and 3b, for example. The sensor module 34 is in the form of an armband 34a comprising embedded electrodes 34b. The portable module 31 may comprise processing unit configured to automatically detect symptoms of Parkinson's disease and indicate right timing for taking medication. In FIG. 3c, the module 31 has a receptacle for a head set plugin. The module 31 is configured to output an alarm sound or an audio comment based on the detected symptoms. Through an earphone connected to the user's ear as shown in FIG. 3c, the module 31 is able to prompt the user to take the medication at the right time.

The above-described EMG measurement setup for detecting symptoms of Parkinson's disease may be set to monitor a person for several days, for example. A reference EMG database comprising reference data may be used to determine a reference level indicating normal behaviour. By collecting EMG data and detecting changes in indicative parameters after days of recordings, the above-described configuration and method may also be used for early detection of Parkinson symptoms, years before the symptoms are disease is visible to bare eye. The reference EMG database may also be taught to link characteristics of the received EMG data to certain parameters of the monitored persons, such as gender, age, weight, illnesses, blood pressure, blood sugar, etc. With a portable monitoring module according to the present disclosure, the amount of medication required can be minimized as the module can provide reliable information on the present condition of the person.

All of the above-described three aspects of monitoring module may be performed with a single portable monitoring module according to the present disclosure. In the following, an embodiment of such a module is discussed in more detail.

Figure 5:
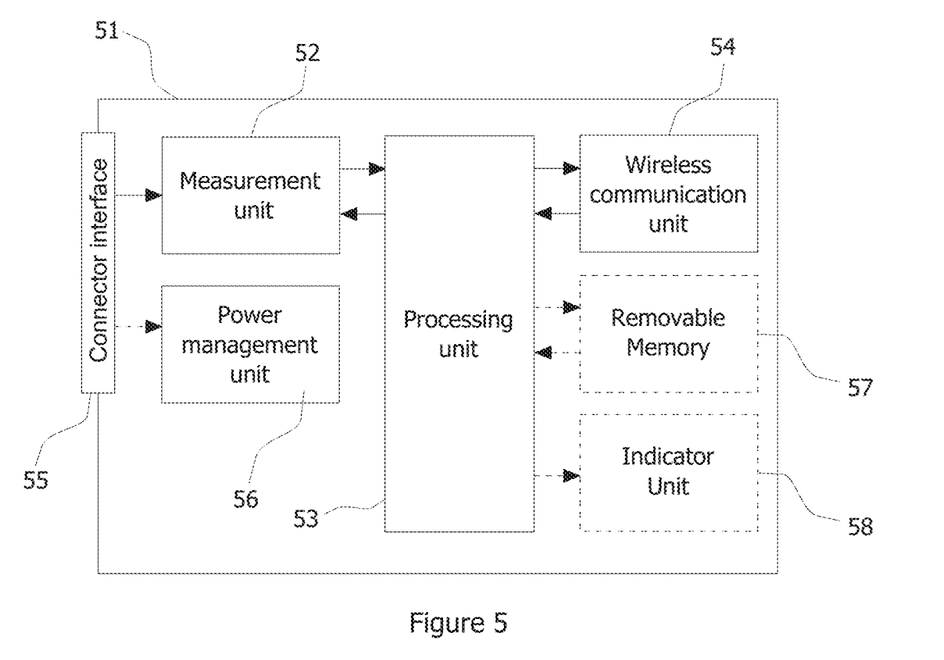
FIG. 5 shows a simplified block diagram of an exemplary embodiment of a portable monitoring module according to the present disclosure.

FIG. 5 shows a simplified block diagram of an exemplary embodiment of a portable monitoring module according to the present disclosure. In FIG. 5, the portable monitoring module 51 comprises a measurement unit 52, a processing unit 53, a wireless communications unit 54, a connector interface 55, and a power management unit 56. The module 51 may further comprise a removable memory 57 and/or an indicator unit 58 generating a visual or audio alarm.

The measurement unit 52 may comprise one or more signal amplifiers and one or more AD-converters, for example. The gain and/or anti-aliasing filtering of the signal amplifier and the sampling rate of the A/D converter may be configurable during in response to a selection signal. For example, the processing unit 53 may select the suitable gain, filtering and/or sample rate for the measurement unit 52 on the basis of the monitored electrical biosignal. Further, the measurement unit 52 may be configured to measure different configurations of measurement channels, and may therefore comprise selection electronics for selecting one or more active channels to be measured.

The biosignals may be measured with electrodes that are connected to the signal amplifiers through the connector interface 55 which serves as a physical interface for forming a galvanic connection to measurement electrodes. The electrodes may be separate, disposable electrodes, or they may be embedded to a sensor module in the form of a head band or armband, for example. The connector interface 55 may comprise at least one physical connector to which a counter connector of a sensor module is detachably attached. In the context of the present disclosure, a connector and its counter connector may be a plug and a receptacle, respectively, or the other way around, for example. In some embodiments, a standard USB plug or receptacle may form the connector interface 55 or a part of the connector interface 55. The connector interface 55 may comprise a plurality of connectors for interfacing with different sensor modules, i.e. forming a galvanic connection with the electrodes of the sensor module. Based on the selected biosignal type to be monitored, the selection electronics of the measurement unit 52 may form different configurations of connections between the measurement unit 52 and one or more connectors in the connector interface 55.

In some embodiments, the connector interface 55 may be configured such that, when the portable monitoring module 51 is attached to a sensor module, the connector interface provides sufficient mechanical support so that monitoring module remains closely fastened to the sensor module regardless of the movements of the user.

The processing unit 53 may comprise a computing device, such as a processor, an FPGA or ASIC, coupled with a memory. The processing unit 53 is configured to detect indicator patterns within the biosignal data as described above. The indication patterns may represent atrial fibrillation (or other arrhythmias of heart), epileptic seizures, and/or tremors caused by Parkinson's disease, for example. In order to be able to store sufficient amount of biosignal data for further analysis, part of the available memory may be on a removable memory. For example, the portable monitoring module 51 may comprise a memory slot for an optional, removable memory card. FIG. 5 shows an optional removable memory 57 that may be a 1 GB SD memory card, for example.

The wireless communications unit 54 may be a Bluetooth module or a WLAN (Wireless Local Area Network) module, for example. The processing unit 53 may be configured to send indication signals (indicating that a pattern has been detected in the measurement data of the monitored biosignal) via the wireless communications unit 54 to be received by a validation unit. Together with the indication signals, the processing unit may send sequence of samples related to the detected pattern to the validation unit. In response, the processing unit 53 may receive control information originating from the validation unit or a handheld computing device communicating wirelessly with the module 51. For example, the processing unit may receive control information regarding indication limits and other setup parameters related to the monitoring algorithms that are used for detecting possible biosignal events.

The power management unit 56 in FIG. 5 may comprise a battery that provides the operational power for the whole module 51. The power management unit 56 may be connected to the connector interface in order to provide a route for wired charging of the battery. For example, the power management unit may be configured to charge the battery through a USB interface that may form a part of the connector interface in some embodiments. In some embodiments, the USB interface may have dual-use: it may act as an interface for attaching measurement electrodes and it may also be used for charging the battery. In some embodiments, the power management unit 56 may also comprise electronics for implementing wireless charging of the battery.

The indicator unit 58 may be a visual indicator in the form of LED/LEDs or a display. Alternatively, or in addition, the indicator unit 58 may be configured to generate an indication in the form of audio output. The module 51 may generate the audio output to an audio receptacle (e.g. socket) to which an earphone or headset plug can be connected. The audio output may be in the form of alarm sound or other audio feedback, such as voice recordings or computer-generated voiced announcements. The visual or audio indications may be generated on the portable monitoring module 51, and/or the monitoring module 51 may receive alerts and other information to be displayed or voiced from an external system, such as the validation system.

Figure 6:
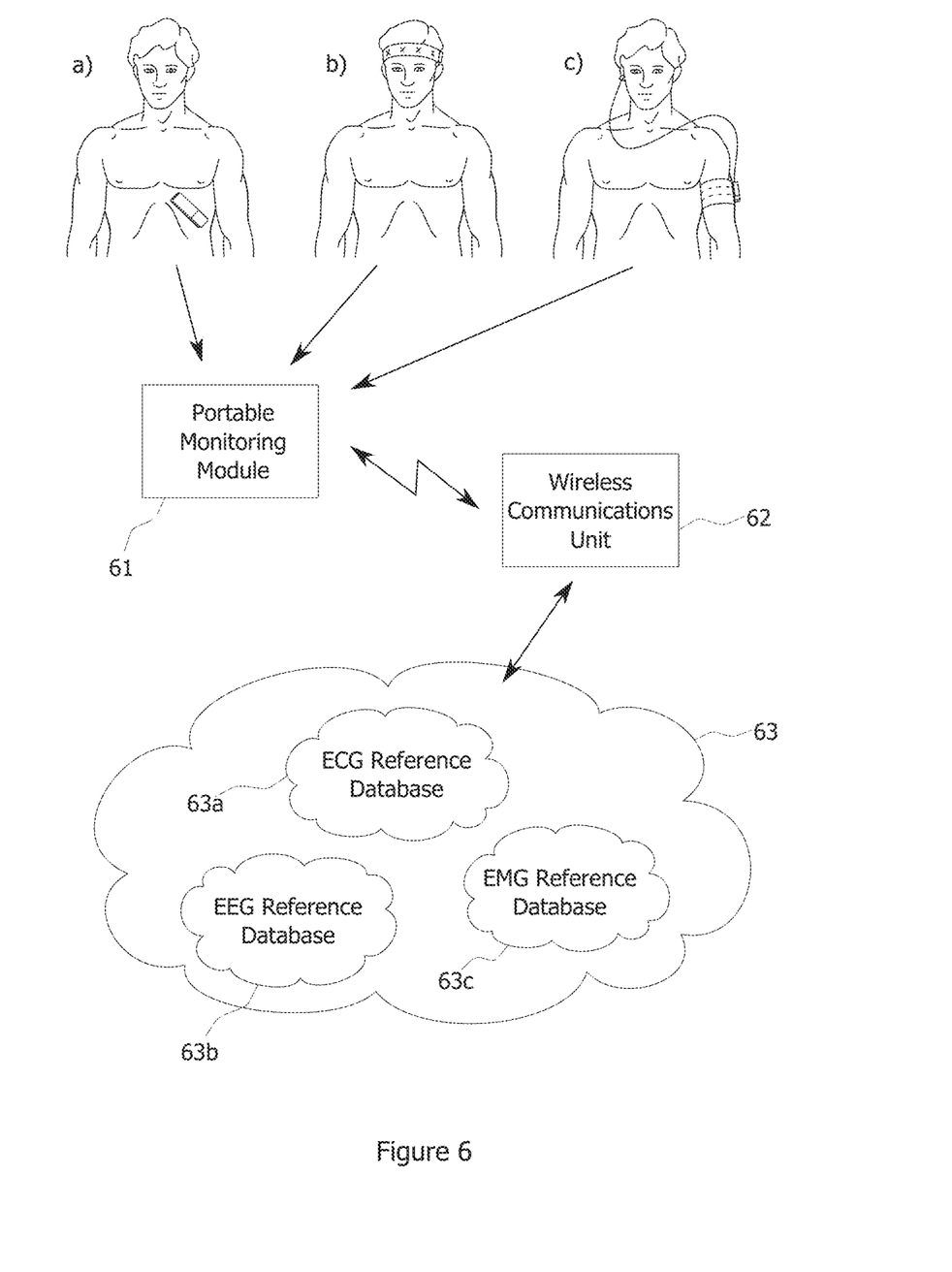
FIG. 6 shows a measurement system with a portable monitoring module according to the present disclosure.

In the following, a measurement system with a portable monitoring module according to the present disclosure is discussed in more detail. FIG. 6 shows a simplified diagram of such measurement system. In FIG. 6, a portable monitoring module 61 according to the present disclosure may be configured to measure three different biosignal measurement options. The portable monitoring module may be similar to the module of FIG. 5, for example. The module 61 communicates wirelessly with a wireless communication unit 62 which, in turn, communicates with a validation system 63. In FIG. 6, the validation system 63 is shown as a cloud computing system that comprises reference databases 63a to 63c for different types of biosignals.

Three different biosignal measurement options a) to c) are shown in the top of the FIG. 6: option a) represents an ECG measurement; option b) represents an EEG measurement; and option c) represents an EMG measurement. The options a) to c) may correspond with the embodiments of FIGS. 3a to 3c, for example. However, the measurement configurations are not limited to the configurations described in FIG. 6. For example, a portable monitoring module according to the present disclosure may measure ECG from an electrode attached below collar bone or from an electrode band in the form of a chest belt. In a similar manner, different configurations of electrodes may be used for EEG. EMG may be measured from either arm or leg, and the electrodes may be in the form of sensor module that comprises an electrode band wrapped around the limb or disposable electrodes attached to skin with an adhesive, for example.

As discussed in relation to the first, second, and third aspect of a portable monitoring module according to the present disclosure, the monitoring module 61 may send indication signals and biosignal data to the communications device 62 that may forward said information to the validation system 63. In some embodiments, the communications device 62 may be a wireless (internet) router that receives data from the portable monitoring module 61 and simply relays it forward unchanged. Alternatively, the wireless communication device 62 in FIG. 6 may be a handheld device, such as a tablet computer or a smart phone, for example. The monitoring module 61 may be paired with the handheld device via Bluetooth, for example. The handheld device, acting as the communications device 62, may relay data unchanged to the validation system 63 or it provide the data with supplemental information, such as personal information identifying the monitored person and his/her location (determined with GPS module integrated to the handheld device). The handheld device may utilize a cellular network or WLAN for sending the data to the validation system 63.

The validation system 63 may be configured to analyse the received biosignal data and confirm the presence (or lack of presence) of a condition (indicated by the monitoring module 61) within the data. At the same time, the validation system 63 may add the received data to a reference database to be utilized in other analyses. For example, the validation system 63 may make predictions on the basis of the gathered data based on how the frequency and intensity of the events have developed over time, for example.

Some simpler embodiments of the validation system 63 may require with only a moderate amount of calculating power. In these cases, the validation system may be implemented directly on a handheld device that acts as the communication device 62. However, when high calculating power is required or a large amount of biosignal data is involved, the validating system may be implemented as a cloud computing system as shown in FIG. 6.

A validation system 63 implemented as a cloud service, i.e. as a cloud computing system, can provide easy access to real time data for medical personnel with mobile tools, which may be implemented in the form of applications on a handheld device, for example. The accessible data may be raw biosignal data or it may be automatically pre-screened, which can help with managing with the workloads of the medical personnel. With the high calculation power potential of a cloud service, interpretation services can also be provided, which can reduce the time for deciding the correct care.

In FIG. 6, the validation system 6 comprises a plurality of reference databases 63a to 63c. When it is possible to compare the biosignal data received from the portable monitoring module 61 with a reference database, the reliability of the system can be further improved. Each biosignal may have its own reference database for example, and each reference database may receive data from monitoring modules of different persons. The databases 63a to 63c may be taught to link certain characteristics of the received biosignal data to certain parameters of the monitored persons, such as gender, age, weight, illnesses, blood pressure, blood sugar, etc. The information provided by the portable monitoring module and the information provided by the validation system and/or the reference database help making right diagnosis based on the findings and providing the correct medication or other steps early on.

It is obvious to a person skilled in the art that the inventive concept can be implemented in various ways. The invention and its embodiments are not limited to the examples described above but may vary within the scope of the claims.

The invention claimed is:

1. A portable monitoring module for monitoring a plurality of electrical biosignals of a person, wherein the portable monitoring module comprises:
   a measurement unit configured to measure a plurality of different types of electrical biosignals with at least two electrodes galvanically connected to the measurement unit, said measurement unit comprising a signal amplifier and an A/D-converter with a programmable sample rate, and said signal amplifier comprising at least one of a programmable antialiasing filter and a programmable gain;
   a wireless communication unit; and
   a processing unit configured to
      select a biosignal type to be monitored from a list of electrical biosignal types supported by the monitoring module, wherein the list of biosignal types includes electrocardiography (ECG), electroencephalography (EEG), and electromyography (EMG),
      set up the signal amplifier and the A/D converter filter and the sample rate based on the selected measurement,
      store samples of biosignal data generated by the measurement unit,
      detect an indicator pattern within the biosignal data, wherein the indicator pattern represents an indication of a possible event of the selected biosignal type, and
      when the indicator pattern is detected, send a set of biosignal data via the wireless communications unit to be received by a validation system, wherein the set of biosignal data represents a sequence of samples of biosignal data related to the detected indicator pattern, and wherein the validation system confirms the presence of the event in the received set of biosignal data.

2. The portable monitoring module according to claim 1, wherein the monitoring module is configured to monitor EEG of the person,
   and the detecting of the indicator pattern comprises detecting a change in the EEG data in order to determine presence of an epileptic seizure, wherein the change in the EEG data is in the form of a change in an amplitude, rate of change or periodicity of a measured EEG signal.

3. The portable monitoring module according to claim 1, wherein the monitoring module is configured to monitor EMG of the person, and the detecting of the indicator pattern comprises detecting a change in monotonicity of the EMG data in order to detect a tremor caused by Parkinson's disease.

4. The portable monitoring module according to claim 1, wherein the monitoring module is configured to monitor ECG of the person, and the detecting of the indicator pattern comprises, for a sequence of successive samples of ECG data, determining intervals between QRS complexes within the samples of ECG data, calculating deviations between each two successive intervals, calculating a cumulative sum of the deviations, and indicating a possible arrhythmias if the cumulative sum exceeds a set limit.

5. The portable monitoring module according to claim 4, wherein the monitoring module is further configured to monitor EEG of the person, and the detecting of the indicator pattern comprises detecting a change in the EEG data in order to determine presence of an epileptic seizure, wherein the change in the EEG data is in the form of a change in an amplitude, rate of change or periodicity of a measured EEG signal.

6. The portable monitoring module according to claim 5, wherein the monitoring module is further configured to monitor EMG of the person, and the detecting of the indicator pattern comprises detecting a change in monotonicity of the EMG data in order to detect a tremor caused by Parkinson's disease.

7. A measurement arrangement for monitoring a plurality of electrical biosignals of a person, comprising:

a portable monitoring module, comprised of a measurement unit, a wireless communication unit, and a processing unit, the measurement unit configured to measure a plurality of different types of electrical biosignals with at least two electrodes galvanically connected to the measurement unit, said measurement unit comprising a signal amplifier and an A/D-converter with a programmable sample rate, and said signal amplifier comprising at least one of a programmable antialiasing filter and a programmable gain, and the processing unit configured to select a biosignal type to be monitored from a list of electrical biosignal types supported by the monitoring module, wherein the list of biosignal types includes electrocardiography (ECG), electroencephalography (EEG), and electromyography (EMG), set up the signal amplifier and the A/D converter filter and the sample rate based on the selected measurement, store samples of biosignal data generated by the measurement unit, detect an indicator pattern within the biosignal data, wherein the indicator pattern represents an indication of a possible event of the selected biosignal type, and when the indicator pattern is detected, send a set of biosignal data via the wireless communications unit to be received by a validation system, wherein the set of biosignal data represents a sequence of samples of biosignal data related to the detected indicator pattern, and wherein the validation system confirms the presence of the event in the received set of biosignal data; and a communications device configured to wirelessly receive the set of biosignal data from the portable monitoring module and to send the set of biosignal data to a validation system, wherein the validation system is configured to confirm the presence of the event in the received set of biosignal data.

8. The measurement arrangement according to claim 7, wherein the monitoring module is configured to monitor ECG of the person, and the detecting of the indicator pattern comprises, for a sequence of successive samples of ECG data, determining intervals between QRS complexes within the samples of ECG data, calculating deviations between each two successive intervals, calculating a cumulative sum of the deviations, and indicating a possible arrhythmias if the cumulative sum exceeds a set limit.

9. The measurement arrangement according to claim 8, wherein the monitoring module is further configured to monitor EEG of the person, and the detecting of the indicator pattern comprises detecting a change in the EEG data in order to determine presence of an epileptic seizure, wherein the change in the EEG data is in the form of a change in an amplitude, rate of change or periodicity of a measured EEG signal.

10. The measurement arrangement according to claim 9, wherein the monitoring module is further configured to monitor EMG of the person, and the detecting of the indicator pattern comprises detecting a change in monotonicity of the EMG data in order to detect a tremor caused by Parkinson's disease.

11. A monitoring method for monitoring an electrical biosignal of a person, the method comprising:

measuring the electrical biosignal with a portable monitoring module that includes each of a measurement unit configured to measure a plurality of different types of electrical biosignals with at least two electrodes galvanically connected to the measurement unit, said measurement unit comprising a signal amplifier and an A/D-converter with a programmable sample rate, and said signal amplifier comprising at least one of a programmable antialiasing filter and a programmable gain, a wireless communication unit, and a processing unit configured to select a biosignal type to be monitored from a list of electrical biosignal types supported by the monitoring module, wherein the list of biosignal types includes electrocardiography (ECG), electroencephalography (EEG), and electromyography (EMG), set up the signal amplifier and the A/D converter filter and the sample rate based on the selected measurement, store samples of biosignal data generated by the measurement unit, detect an indicator pattern within the biosignal data, wherein the indicator pattern represents an indication of a possible event of the selected biosignal type, and when the indicator pattern is detected, send a set of biosignal data via the wireless communications unit to be received by a validation system, wherein the set of biosignal data represents a sequence of samples of biosignal data related to the detected indicator pattern, and wherein the validation system confirms the presence of the event in the received set of biosignal data.

* * * * *